United States Patent
Heiliger

(10) Patent No.: US 11,896,291 B2
(45) Date of Patent: Feb. 13, 2024

(54) ELECTRICALLY-INSULATIVE SHAFTS, METHODS OF MANUFACTURING ELECTRICALLY-INSULATIVE SHAFTS, AND ENERGY-BASED SURGICAL INSTRUMENTS INCORPORATING ELECTRICALLY-INSULATIVE SHAFTS

(71) Applicant: COVIDIEN LP, Mansfield, MA (US)

(72) Inventor: Zachary S. Heiliger, Nederland, CO (US)

(73) Assignee: Covidien LP, Mansfield, MA (US)

( * ) Notice: Subject to any disclaimer, the term of this patent is extended or adjusted under 35 U.S.C. 154(b) by 1609 days.

(21) Appl. No.: 16/024,989

(22) Filed: Jul. 2, 2018

(65) Prior Publication Data

US 2020/0000512 A1 Jan. 2, 2020

(51) Int. Cl.
  *A61B 18/14* (2006.01)
  *A61B 17/29* (2006.01)
  *A61B 17/295* (2006.01)
  *A61B 18/00* (2006.01)

(52) U.S. Cl.
  CPC ........ *A61B 18/1445* (2013.01); *A61B 17/295* (2013.01); *A61B 17/2909* (2013.01); *A61B 2017/2902* (2013.01); *A61B 2017/294* (2013.01); *A61B 2018/1455* (2013.01)

(58) Field of Classification Search
  CPC .............. A61B 18/1445; A61B 17/295; A61B 17/2909; A61B 2017/294; A61B 2017/2902; A61B 2018/1455
  See application file for complete search history.

(56) References Cited

U.S. PATENT DOCUMENTS

| | | | |
|---|---|---|---|
| 2,801,633 A | 8/1957 | Ehrlich | |
| 4,311,144 A * | 1/1982 | Harada | ............... A61B 18/1482 606/46 |
| 4,512,343 A | 4/1985 | Falk et al. | |
| 5,100,420 A | 3/1992 | Green et al. | |
| 5,242,456 A | 9/1993 | Nash et al. | |
| 5,312,401 A * | 5/1994 | Newton | .................. A61B 18/14 606/46 |
| 5,342,359 A | 8/1994 | Rydell | |
| 5,368,600 A | 11/1994 | Failla et al. | |
| 5,383,471 A | 1/1995 | Funnell | |

(Continued)

FOREIGN PATENT DOCUMENTS

| | | |
|---|---|---|
| AU | 2011253698 A1 | 12/2011 |
| CN | 201299462 Y | 9/2009 |

(Continued)

*Primary Examiner* — Joseph A Stoklosa
*Assistant Examiner* — Annie L Shoulders
(74) *Attorney, Agent, or Firm* — Carter, DeLuca & Farrell LLP

(57) ABSTRACT

An electrically-insulative shaft for an energy-based surgical instrument includes an outer tube formed from an electrically-insulative material, an inner tube formed from an electrically-insulative material, and an intermediate tube disposed between the outer and inner tubes. The intermediate tube is formed from an electrically-conductive material. Distal ends of the outer and inner tubes extend beyond a distal end of the intermediate tube and are joined to one another to enclose the distal end of the intermediate tube therebetween.

22 Claims, 6 Drawing Sheets

(56) References Cited

U.S. PATENT DOCUMENTS

| | | | |
|---|---|---|---|
| 5,456,684 A | 10/1995 | Schmidt et al. | |
| 5,578,052 A | 11/1996 | Koros et al. | |
| 5,707,392 A | 1/1998 | Kortenbach | |
| H1745 H | 8/1998 | Paraschac | |
| 5,830,214 A | 11/1998 | Flom et al. | |
| 6,117,158 A | 9/2000 | Measamer et al. | |
| H1904 H | 10/2000 | Yates et al. | |
| 6,387,094 B1 | 5/2002 | Eitenmuller | |
| H2037 H | 7/2002 | Yates et al. | |
| 6,733,514 B2 | 5/2004 | Miser | |
| 6,758,857 B2 | 7/2004 | Cioanta et al. | |
| 7,103,947 B2 | 9/2006 | Sartor et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinge | |
| D541,938 S | 5/2007 | Kerr et al. | |
| D545,432 S | 6/2007 | Watanabe | |
| 7,232,440 B2 | 6/2007 | Dumbauld et al. | |
| D547,154 S | 7/2007 | Lee | |
| 7,244,257 B2 | 7/2007 | Podhajsky et al. | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,431,730 B2 | 10/2008 | Viola | |
| D582,038 S | 12/2008 | Swoyer et al. | |
| 7,594,313 B2 | 9/2009 | Prakash et al. | |
| 7,641,653 B2 | 1/2010 | Dalla Betta et al. | |
| 7,722,607 B2 | 5/2010 | Dumbauld et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| 7,815,638 B2 * | 10/2010 | Farin | A61B 18/042 606/45 |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 7,896,878 B2 | 3/2011 | Johnson et al. | |
| D649,249 S | 11/2011 | Guerra | |
| D649,643 S | 11/2011 | Allen, IV et al. | |
| D661,394 S | 6/2012 | Romero et al. | |
| 8,246,618 B2 | 8/2012 | Bucciaglia et al. | |
| 8,251,989 B1 * | 8/2012 | Newton | A61B 18/1233 606/34 |
| 8,328,802 B2 | 12/2012 | Deville et al. | |
| 8,758,336 B2 * | 6/2014 | Odell | A61B 18/1233 606/34 |
| 8,920,461 B2 | 12/2014 | Unger et al. | |
| 8,926,610 B2 | 1/2015 | Hafner et al. | |
| 9,113,924 B2 * | 8/2015 | Brannan | A61B 18/1815 |
| 9,358,028 B2 | 6/2016 | Moua et al. | |
| 9,956,032 B1 * | 5/2018 | Cosman | A61B 18/1477 |
| 10,166,069 B2 * | 1/2019 | Tran | B29C 45/14598 |
| 10,898,291 B2 * | 1/2021 | Davies | A61M 25/0127 |
| 2002/0058925 A1 | 5/2002 | Kaplan et al. | |
| 2008/0015566 A1 | 1/2008 | Livneh | |
| 2009/0012520 A1 | 1/2009 | Hixson et al. | |
| 2009/0043304 A1 | 2/2009 | Tetzlaff et al. | |
| 2009/0043305 A1 | 2/2009 | Brodbeck et al. | |
| 2009/0088743 A1 | 4/2009 | Masuda | |
| 2009/0088747 A1 | 4/2009 | Hushka et al. | |
| 2009/0088750 A1 | 4/2009 | Hushka et al. | |
| 2009/0105705 A1 * | 4/2009 | Tan | A61B 18/082 29/428 |
| 2009/0182327 A1 | 7/2009 | Unger | |
| 2009/0254084 A1 | 10/2009 | Naito | |
| 2009/0281477 A1 * | 11/2009 | Mikus | A61B 18/1477 606/41 |
| 2009/0306604 A1 * | 12/2009 | Darmos | A61B 18/1477 606/41 |
| 2010/0097284 A1 * | 4/2010 | Brannan | A61B 18/18 343/793 |
| 2010/0185196 A1 | 7/2010 | Sakao et al. | |
| 2010/0185197 A1 | 7/2010 | Sakao et al. | |
| 2010/0292690 A1 | 11/2010 | Livneh | |
| 2011/0009864 A1 | 1/2011 | Bucciaglia et al. | |
| 2011/0034918 A1 | 2/2011 | Reschke | |
| 2011/0060334 A1 | 3/2011 | Brandt et al. | |
| 2011/0060356 A1 | 3/2011 | Reschke et al. | |
| 2011/0071522 A1 | 3/2011 | Dumbauld et al. | |
| 2011/0087218 A1 | 4/2011 | Boudreaux et al. | |
| 2011/0130757 A1 | 6/2011 | Horlle et al. | |
| 2011/0251606 A1 | 10/2011 | Kerr | |
| 2011/0264093 A1 | 10/2011 | Schall | |
| 2011/0319888 A1 | 12/2011 | Mueller et al. | |
| 2012/0083786 A1 | 4/2012 | Artale et al. | |
| 2012/0330351 A1 | 12/2012 | Friedman et al. | |
| 2013/0165907 A1 | 6/2013 | Attar et al. | |
| 2014/0276797 A1 | 9/2014 | Batchelor et al. | |
| 2016/0166317 A1 * | 6/2016 | Townsend | A61B 18/1482 606/41 |
| 2016/0242661 A1 * | 8/2016 | Fischell | A61B 5/6852 |
| 2017/0050011 A1 * | 2/2017 | Zergiebel | A61M 39/1011 |
| 2017/0112514 A1 * | 4/2017 | Marchand | A61B 17/3415 |

FOREIGN PATENT DOCUMENTS

| | | |
|---|---|---|
| CN | 203736301 U | 7/2014 |
| DE | 2415263 A1 | 10/1975 |
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 4242143 A1 | 6/1994 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 B4 | 3/1999 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009318 U1 | 8/2007 |
| DE | 202007009317 U1 | 10/2007 |
| DE | 10031773 B4 | 11/2007 |
| DE | 202007016233 U1 | 1/2008 |
| DE | 102004026179 B4 | 1/2009 |
| DE | 102008018406 B3 | 7/2009 |
| EP | 1159926 A3 | 3/2003 |
| EP | 1530952 | 5/2005 |
| JP | 61501068 | 9/1984 |
| JP | 1147150 A | 6/1989 |
| JP | 6502328 | 3/1992 |
| JP | 55106 | 1/1993 |
| JP | 0540112 | 2/1993 |
| JP | 0006030945 A | 2/1994 |
| JP | 6121797 A | 5/1994 |
| JP | 6285078 A | 10/1994 |
| JP | 06343644 A | 12/1994 |
| JP | 6511401 | 12/1994 |
| JP | 07265328 A | 10/1995 |
| JP | H0856955 | 5/1996 |
| JP | 08252263 A | 10/1996 |
| JP | 8289895 A | 11/1996 |
| JP | 8317934 A | 12/1996 |
| JP | H0910223 A | 1/1997 |
| JP | 9122138 A | 5/1997 |
| JP | 0010000195 A | 1/1998 |

(56) References Cited

FOREIGN PATENT DOCUMENTS

| | | |
|---|---|---|
| JP | H1024051 A | 1/1998 |
| JP | 10155798 A | 6/1998 |
| JP | 11070124 A | 3/1999 |
| JP | 11169381 A | 6/1999 |
| JP | 11192238 A | 7/1999 |
| JP | 11244298 A | 9/1999 |
| JP | 2000102545 A | 4/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001003400 | 4/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005237574 A | 9/2005 |
| JP | 2005253789 A | 9/2005 |
| JP | 2006015078 A | 1/2006 |
| JP | 2006501939 A | 1/2006 |
| JP | 2006095316 A | 4/2006 |
| JP | 2006116320 A | 5/2006 |
| JP | 2007098136 A | 4/2007 |
| JP | 2008246222 A | 10/2008 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A2 | 6/2002 |
| WO | 2005110264 A3 | 4/2006 |

\* cited by examiner

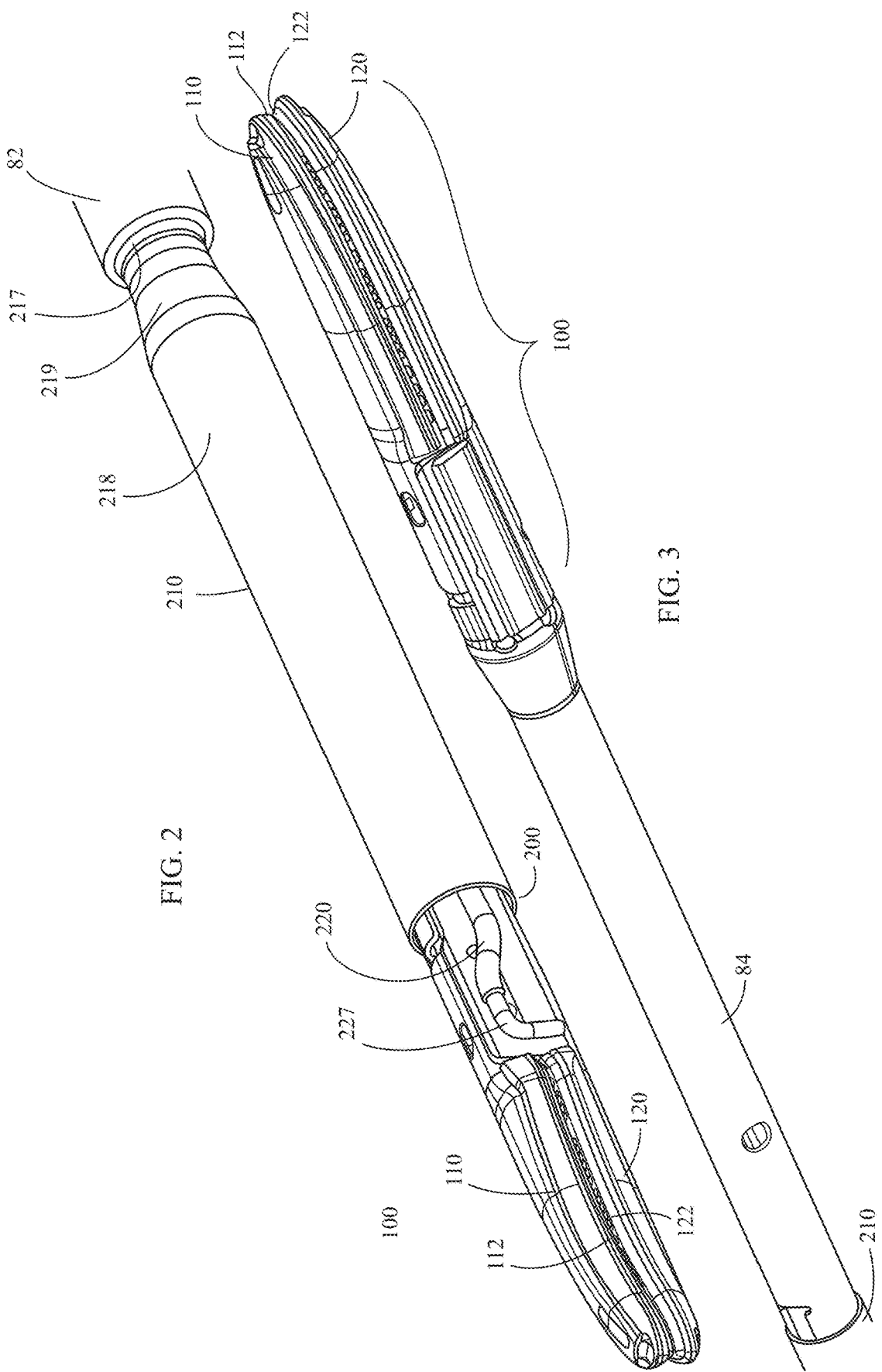

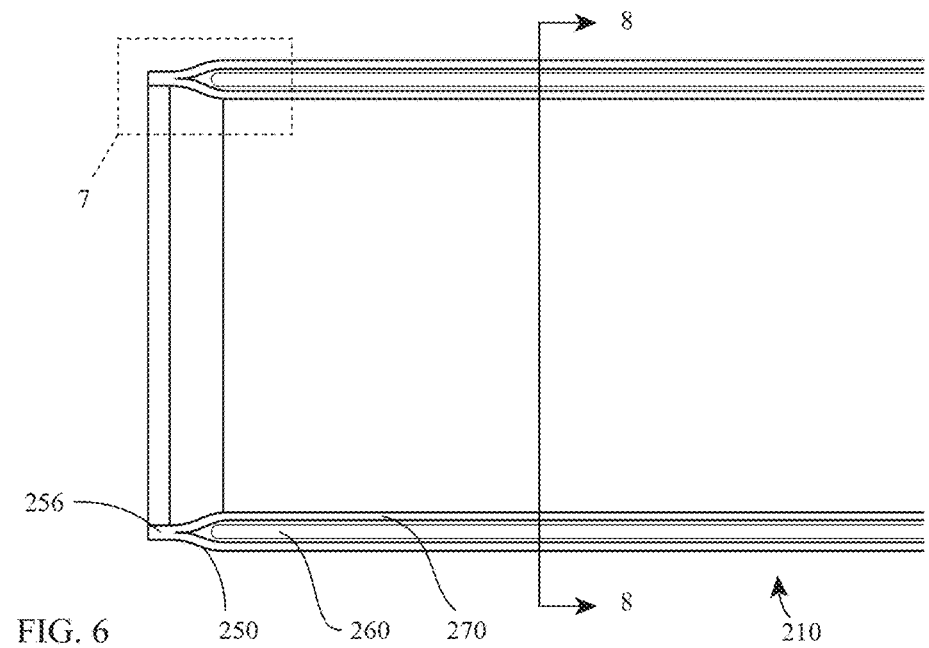
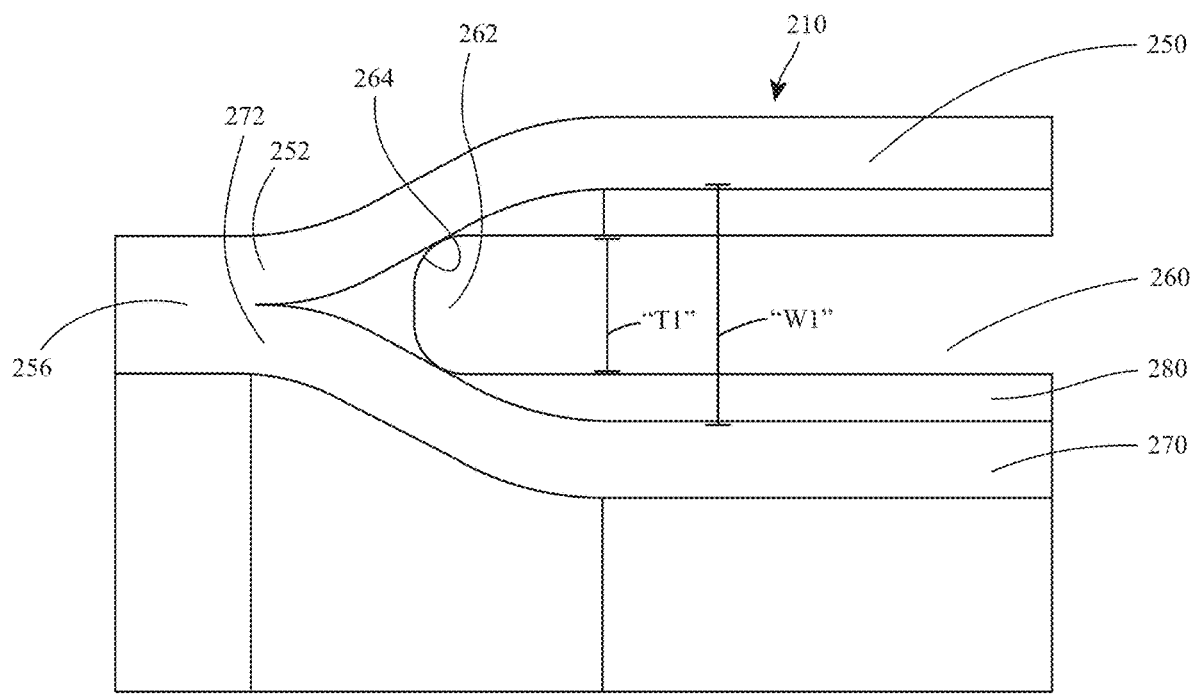

ELECTRICALLY-INSULATIVE SHAFTS, METHODS OF MANUFACTURING ELECTRICALLY-INSULATIVE SHAFTS, AND ENERGY-BASED SURGICAL INSTRUMENTS INCORPORATING ELECTRICALLY-INSULATIVE SHAFTS

BACKGROUND

Technical Field

The present disclosure relates to energy-based surgical instruments and, more particularly, to electrically-insulative shafts for energy-based surgical instruments, methods of manufacturing the same, and energy-based surgical instruments incorporating the same.

Background of Related Art

Bipolar surgical instruments typically include two generally opposing electrodes charged to different electric potentials to selectively apply energy to tissue. Bipolar electrosurgical forceps, for example, utilize both mechanical clamping action and electrical energy to treat, e.g., cauterize, coagulate, desiccate, and/or seal, tissue.

Monopolar surgical instruments, on the other hand, include an active electrode, and are used in conjunction with a remote return electrode, e.g., a return pad, to apply energy to tissue. Monopolar instruments have the ability to rapidly move through tissue and dissect through narrow tissue planes.

Multi-function energy-based surgical instruments may incorporate various different energy modalities such as, for example, both bipolar and monopolar features. As such, these multi-function instruments obviate the need to alternatingly remove and insert bipolar and monopolar instruments in favor of one another.

Electrically-insulative shafts are commonly utilized in bipolar surgical instruments, monopolar surgical instruments, multi-function surgical instruments, and other energy-based surgical instruments configured to apply or receive energy. Electrically-insulative shafts are widely utilized because they inhibit capacitive coupling and other unwanted electrical interactions, thus protecting the instrument, patient, and surgical team.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

Provided in accordance with aspects of the present disclosure is an electrically-insulative shaft for an energy-based surgical instrument including an outer tube formed from an electrically-insulative material, an inner tube formed from an electrically-insulative material, and an intermediate tube disposed between the outer and inner tubes. The intermediate tube is formed from an electrically-conductive material. Distal ends of the outer and inner tubes extend beyond a distal end of the intermediate tube and are joined to one another to enclose the distal end of the intermediate tube therebetween.

In an aspect of the present disclosure, the distal ends of the outer and inner tubes are joined along a longitudinally-extending joint. Alternatively, the distal ends of the outer and inner tubes may be joined along a transversely-extending joint.

In another aspect of the present disclosure, an O-ring is disposed between the outer and inner tubes and between the distal end of the intermediate tube and the joined distal ends of the outer and inner tubes.

In yet another aspect of the present disclosure, a radial space is defined between at least one of the intermediate tube and the inner tube or the intermediate tube and the outer tube. Alternatively, the intermediate tube may substantially fully occupy the annular gap between the inner and outer tubes.

In still another aspect of the present disclosure, the outer and inner tubes are formed from PTFE and/or the intermediate tube is formed from stainless steel.

A surgical instrument provided in accordance with aspects of the present disclosure includes a housing, at least one electrode operably coupled to the housing and configured to supply energy to tissue, and an electrically-insulative shaft extending at least partially between the housing and the at least one electrode. The electrically-insulative shaft may be configured similar to any of the aspects detailed above or otherwise described herein.

In an aspect of the present disclosure, the at least one electrode includes a monopolar electrode. Alternatively or additionally, the at least one electrode includes a pair of bipolar electrodes.

A method of manufacturing an electrically-insulative shaft for a surgical instrument provided in accordance with aspects of the present disclosure includes providing an electrically-insulative outer tube, an electrically-insulative inner tube, and an electrically-conductive intermediate tube. The method further includes joining distal ends of the outer tube and inner tube with one another to form a joint and inserting the intermediate tube into an annular gap defined between the outer and inner tubes.

In an aspect of the present disclosure, the distal ends of the outer tube and inner tube are joined with one another to form the joint prior to inserting the intermediate tube into the annular gap. Alternatively, the distal ends of the outer tube and inner tube are joined with one another to form the joint after inserting the intermediate tube into the annular gap.

In another aspect of the present disclosure, the distal ends of the outer tube and inner tube are joined with one another to form the joint such that the joint extends in one of a longitudinal direction or a transverse direction.

BRIEF DESCRIPTION OF THE DRAWINGS

Various aspects of the present disclosure are described herein with reference to the drawings wherein like reference numerals identify similar or identical elements and:

FIG. 2 is an enlarged, perspective view of the area of detail indicated as "2" in FIG. 1;

FIG. 3 is an enlarged, perspective view of the area of detail indicated as "2" in FIG. 1 from the opposite side as illustrated in FIG. 2, with portions removed;

FIG. 6 is a longitudinal, cross-sectional view of a distal end portion of an electrically-insulative shaft provided in accordance with the present disclosure and configured for use with the surgical instrument of FIG. 1;

FIG. 7 is an enlarged view of the area of detail indicated as "7" in FIG. 6;

DETAILED DESCRIPTION

Figure 1:
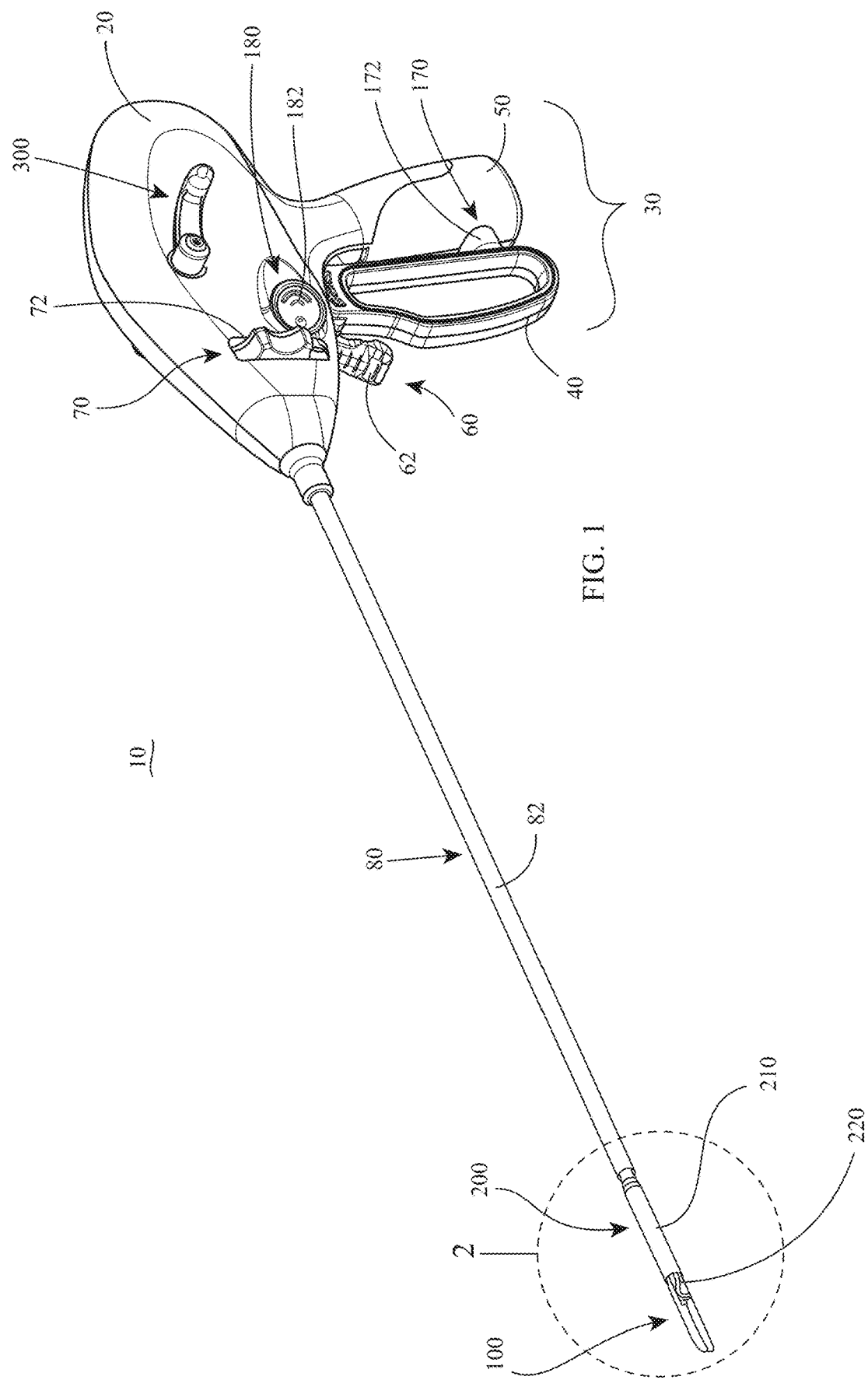
FIG. 1 is a perspective view of an endoscopic surgical instrument provided in accordance with the present disclosure.

The present disclosure provides electrically-insulative shafts for energy-based surgical instruments, methods of manufacturing electrically-insulative shafts, and energy-based surgical instruments including electrically-insulative shafts. Thus, although the present disclosure is shown and described with respect to endoscopic surgical instrument 10 (FIG. 1), the aspects and features of the present disclosure are equally applicable for use with any suitable energy-based surgical instrument or portion(s) thereof. Obviously, different connections and considerations apply to each particular instrument and the assemblies and/or components thereof; however, the aspects and features of the present disclosure remain generally consistent regardless of the particular instrument, assemblies, and/or components provided.

Referring generally to FIGS. 1-5, endoscopic surgical instrument 10 is configured to operate in both a bipolar mode, e.g., for grasping, treating, and/or mechanically dissecting tissue, and a monopolar mode, e.g., for treating and/or electrically/electromechanically dissecting tissue. Instrument 10 generally includes a housing 20, a handle assembly 30, a trigger assembly 60, a rotation assembly 70, an elongated shaft assembly 80, an end effector assembly 100, a drive assembly 140, a knife assembly 160, bipolar and monopolar activation assemblies 170, 180, respectively, a monopolar assembly 200, and a deployment and retraction mechanism 300. Elongated shaft assembly 80 extends distally from housing 20 and supports end effector assembly 100 at a distal end thereof. Drive assembly 140 operably couples handle assembly 30 with end effector assembly 100 to enable selective manipulation of jaw members 110, 120 of end effector assembly 100. Knife assembly 160 is operably coupled with trigger assembly 60 to enable selective translation of knife 164 of knife assembly 160 relative to end effector assembly 100. Monopolar assembly 200 is operably coupled with deployment and retraction mechanism 300 to enable selective deployment and retraction of monopolar assembly 200. Rotating assembly 70 is operably coupled to elongated shaft assembly 80 and enables selective rotation of elongated shaft assembly 80, drive assembly 140, trigger assembly 60, end effector assembly 100, and monopolar assembly 200 relative to housing 20. Bipolar and monopolar activation assemblies 170, 180 enable the appropriate energy to be selectively delivered to end effector assembly 100 and monopolar assembly 200, respectively.

Instrument 10 may also include an electrosurgical cable (not shown) that connects instrument 10 to a generator (not shown) or other suitable power source, although instrument 10 may alternatively be configured as a battery-powered instrument. The electrosurgical cable (not shown) includes wires (not shown) extending therethrough that have sufficient length to extend through housing 20 and/or elongated shaft assembly 80 in order to provide energy to at least one of the electrically-conductive surfaces 112, 122 of jaw members 110, 120, respectively, of end effector assembly 100, e.g., upon activation of bipolar activation switch 172 of bipolar activation assembly 170 in the bipolar mode of operation. Similarly, one or more of the wires of the electrosurgical cable (not shown) extends through housing 20 and/or elongated shaft assembly 80 in order to provide energy to monopolar assembly 200, e.g., upon activation of either of the monopolar activation switches 182 of monopolar activation assembly 180 in the monopolar mode of operation.

Elongated shaft assembly 80 includes a fixed outer tube 82 configured for engagement with housing 20. Fixed outer tube 82 does not extend distally to end effector assembly 100 but, rather, is spaced-apart therefrom, leaving an exposed section of monopolar assembly 200. Elongated shaft assembly 80 further includes an inner proximal tube 83, an inner distal tube 84, and an inner guide assembly 86 including a plurality of guide components 87 that cooperate to house and/or guide at least a portion of drive assembly 140 knife assembly 160, and monopolar assembly 200. Inner proximal tube 83 engages rotation assembly 70 and inner distal tube 84 engages jaw member 120 while inner guide assembly 86 extends between inner proximal tube 83 and inner distal tube 84. Inner proximal tube 83, inner distal tube 84, and inner guide assembly 86 are rotationally coupled with one another such that rotation of inner proximal tube 83 via rotation of rotation assembly 70 effects corresponding rotation of end effector assembly 100, drive assembly 140, knife assembly 160, and monopolar assembly 200 relative to housing 20 (FIG. 1) and fixed outer tube 82.

Figure 5:
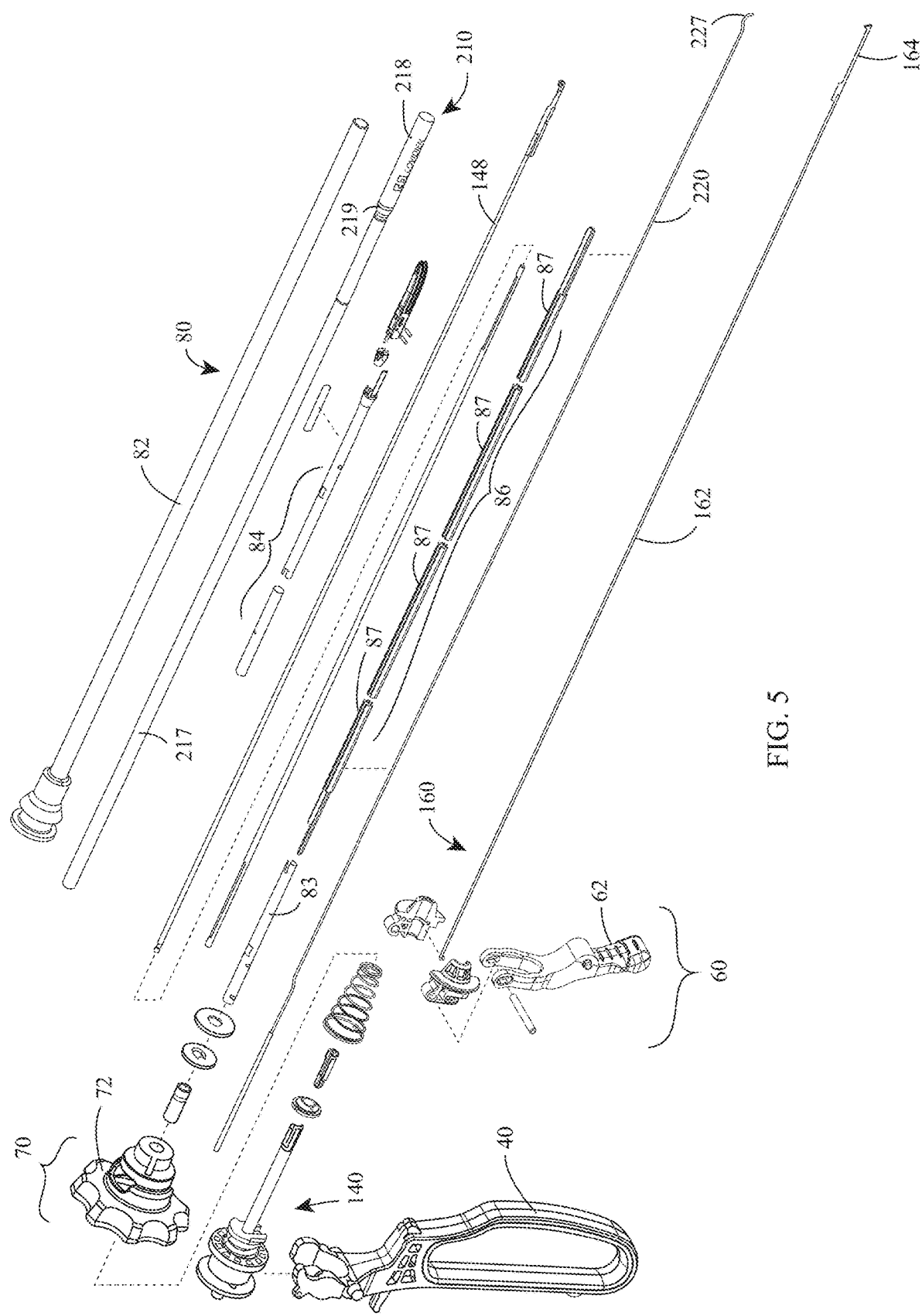
FIG. 5 is an exploded, perspective view of various operable assemblies of the surgical instrument of FIG. 1.
Figure 8:
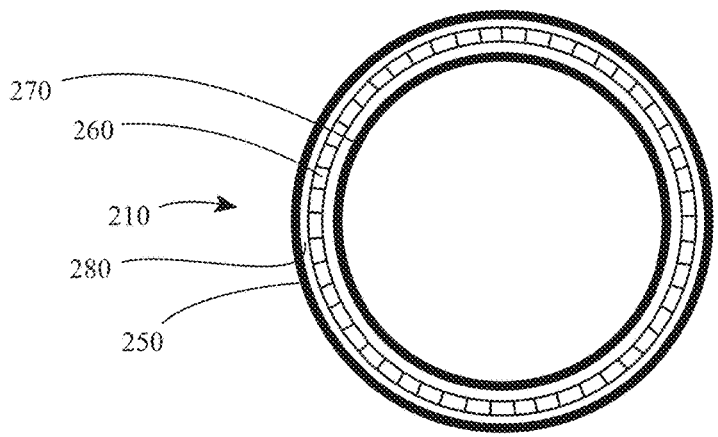
FIG. 8 is a transverse, cross-sectional view taken across section line "8-8" of FIG. 6.

With reference to FIGS. 2, 3, and 5, end effector assembly 100 is disposed at the distal end of elongated shaft assembly 80 and includes opposing jaw members 110, 120 pivotably coupled to one another. Each of the jaw members 110, 120 includes an electrically-conductive surface 112, 122 adapted to connect to the source of energy (not shown) whci is configured to conduct energy through tissue grasped therebetween. End effector assembly 100 defines a bipolar configuration wherein surface 112 is charged to a first electrical potential and surface 122 is charged to a second, different, electrical potential such that an electrical potential gradient is created for conducting energy between surfaces 112, 122 and through tissue grasped therebetween for treating tissue. Bipolar activation switch 172 of bipolar activation assembly 170 (FIG. 1) is operably coupled between the source of energy (not shown) and surfaces 112, 122 via one or more wires (not shown), thus allowing the selective application of energy to surfaces 112, 122 of jaw members 110, 120, respectively, of end effector assembly 100 during the bipolar mode of operation.

End effector assembly 100 is designed as a unilateral assembly, e.g., where jaw member 120 is fixed relative to elongated shaft assembly 80, e.g., jaw member 120 is engaged with inner distal tube 84 of elongated shaft assembly 80, and jaw member 110 is movable relative to elongated shaft assembly 80 and fixed jaw member 120. However, end effector assembly 100 may alternatively be configured as a bilateral assembly, i.e., where both jaw member 110 and jaw member 120 are movable relative to one another and to elongated shaft assembly 80. Further, in some embodiments, a longitudinally-extending knife channel (not shown) may be defined within one or both of jaw members 110, 120 to permit reciprocation of knife 164 therethrough, e.g., upon actuation of a trigger 62 of trigger assembly 60, to cut tissue grasped between jaw members 110, 120.

Figure 4:
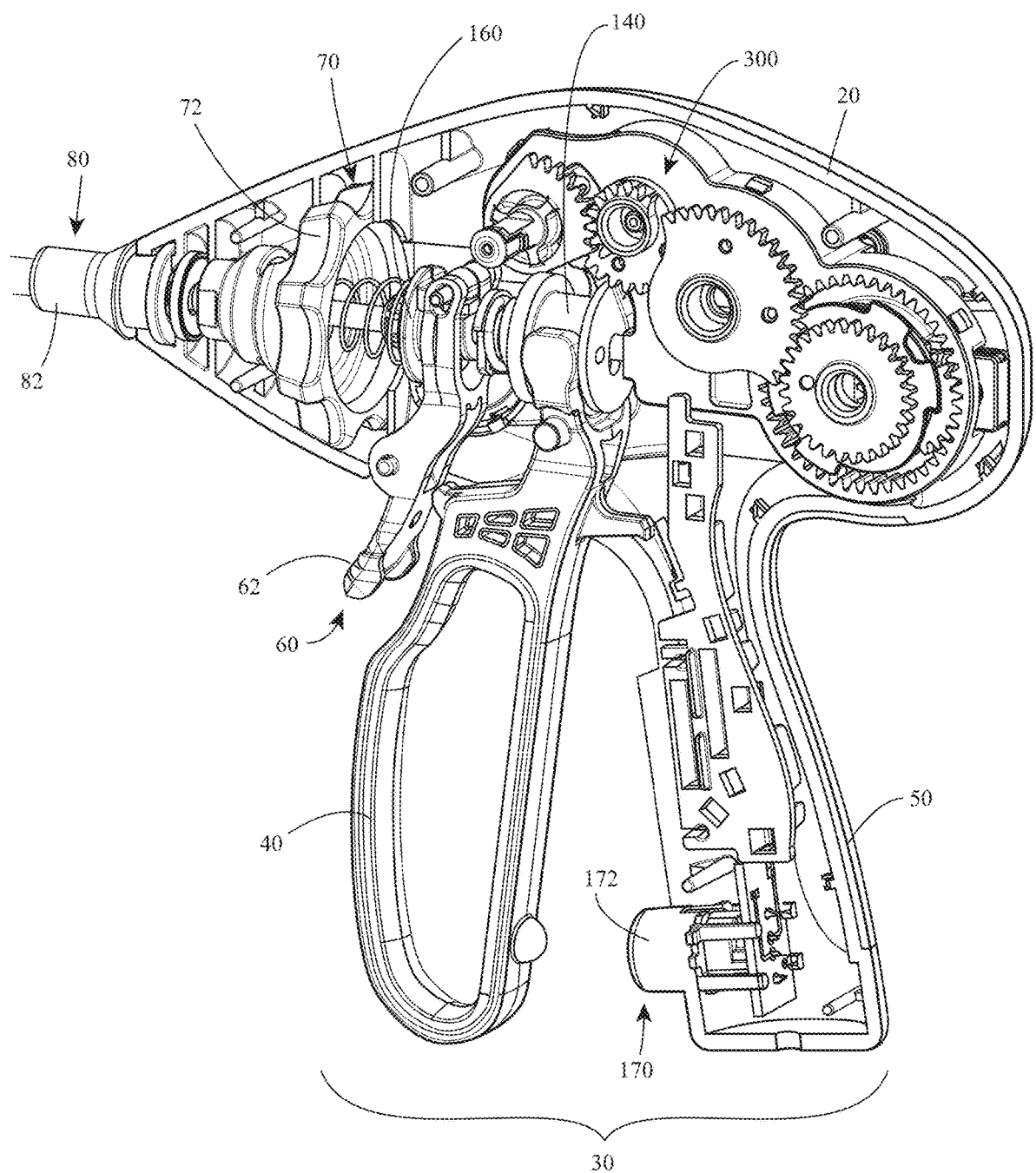
FIG. 4 is a perspective view of the proximal end of the surgical instrument of FIG. 1 with portions removed to illustrate the internal working components thereof.

Referring to FIGS. 1, 4, and 5, handle assembly 30 includes movable handle 40 and a fixed handle 50. Fixed handle 50 is integrally associated with housing 20 and movable handle 40 is movable relative to fixed handle 50 between an initial position, wherein movable handle 40 is spaced-apart from fixed handle 50, and a compressed position, wherein movable handle 40 is compressed towards fixed handle 50.

Referring to FIG. 5, drive assembly 140 operably couples movable handle 40 to jaw member 110. Drive assembly 140, more specifically, includes a drive bar 148 operably coupled to end effector assembly 100 at the distal end of drive bar 148 and operably coupled to movable handle 40 at the proximal end of drive bar 148. Drive bar 148 extends through inner proximal tube 83, inner guide assembly 86, and inner distal tube 84. Translation of drive bar 148 relative to end effector assembly 100 pivots jaw member 110 relative to jaw member 120.

Referring to FIGS. 1, 4, and 5, trigger 62 of trigger assembly 60 is selectively actuatable relative to housing 20 from an un-actuated position to an actuated position. Knife assembly 160 is operably coupled to trigger 62 such that actuation of trigger 62 from the un-actuated position to the actuated position translates knife 164 of knife assembly 160 from a retracted position, wherein knife 164 is disposed proximally of jaw members 110, 120, to an extended position, wherein knife 164 extends at least partially between jaw members 110, 120 and through the knife channel(s) (not shown) thereof to cut tissue grasped between jaw members 110, 120.

Knife assembly 160 includes knife bar 162 and knife 164. Knife bar 162 extends proximally from knife 164 through inner distal tube 84, inner guide assembly 86, and inner proximal tube 83 into housing 20. Within housing 20, knife bar 162 is operably coupled with trigger 62 to operably couple trigger assembly 60 and knife assembly 160 with one another such that, upon actuation of trigger 62 from the un-actuated position to the actuated position, knife 164 is translated distally from the retracted position to the extended position to cut tissue grasped between jaw members 110, 120.

Rotation assembly 70 includes rotation wheel 72 that extends outwardly from housing 20 on either side thereof (see FIG. 1). Rotation wheel 72 is engaged about inner proximal tube 83 of elongated shaft assembly 80 such that, as mentioned above, rotation of rotation wheel 72 effects corresponding rotation of inner proximal tube 83, inner distal tube 84, inner guide assembly 86, end effector assembly 100, drive assembly 140, knife assembly 160, and monopolar assembly 200 relative to housing 20 (FIG. 1) and fixed outer tube 82.

With reference to FIGS. 1-5, monopolar assembly 200 includes an electrically-insulative shaft 210 and an energizable member 220. Electrically-insulative shaft 210 defines a body portion 217, an enlarged-diameter distal portion 218 extending distally from body portion 217, and an annular step 219 disposed therebetween, although other configurations are also contemplated. Electrically-insulative shaft 210 is movable relative to end effector assembly 100 between a storage position, wherein electrically-insulative shaft 210 is disposed proximally of end effector assembly 100, and a use position, wherein electrically-insulative shaft 210 is substantially disposed about end effector assembly 100. Electrically-insulative shaft 210 is described in greater detail below.

Energizable member 220 of monopolar assembly 200 defines a distal tissue-treating portion 227 that is coupled to the source of energy (not shown) and monopolar activation assembly 180 (FIG. 5) via one or more wires (not shown) to function as the active electrode of monopolar assembly 200. Energizable member 220 extends through inner proximal tube 83, inner guide assembly 86, and inner distal tube 84 and into housing 20.

Energizable member 220 is disposed on the inner-edge side of jaw members 110, 120 of end effector assembly 100 and is movable relative thereto between a storage position, wherein distal tissue-treating portion 227 of energizable member 220 is positioned more-proximally, and a use position, wherein distal tissue-treating portion 227 of energizable member 220 extends distally from end effector assembly 100 to facilitate treating tissue therewith. In the use position, electrically-insulative shaft 210 serves to electrically insulate end effector assembly 100 from distal tissue-treating portion 227 of energizable member 220, while distal tissue-treating portion 227 extends distally from end effector assembly 100. Further, in the use position, energy may be supplied to distal tissue-treating portion 227 of energizable member 220, e.g., via activation of either of the activation switches 182 of monopolar activation assembly 180 (FIG. 1), for treating tissue in the monopolar mode of operation.

Referring also to FIGS. 4 and 5, energizable member 220 is engaged with electrically-insulative shaft 210 such that energizable member 220 and electrically-insulative shaft 210 move together between their respective storage and use positions. Further, a proximal end portion of energizable member 220 is operably coupled to deployment and retraction mechanism 300 within housing 20, thus enabling deployment and retraction mechanism 300 to translate electrically-insulative shaft 210 and energizable member 220 between their respective storage positions, collectively the storage condition of monopolar assembly 200, and their respective use conditions, collectively the use condition of monopolar assembly 200.

Electrically-insulative shaft 210 provides sufficient electrical insulation to inhibit capacitive coupling between energizable member 220 and the electrically-conductive surfaces 112, 122 of jaw members 110, 120 as well as any other electrically-conductive components disposed within electrically-insulative shaft 210. Electrically-insulative shaft 210 is also semi-flexible to permit some bending, e.g., up to 35 degrees from the longitudinal axis thereof, without permanent deformation or breaking. The configuration of electrically-insulative shaft 210 and method of manufacturing the same that provides sufficient electrical insulation and also allows for some bending without permanent deformation or breaking is detailed below. However, it is understood that electrically-insulative shaft 210 and the method of manufacturing the same may provide other benefits to a surgical instrument and/or be utilized in a surgical instrument for other purposes.

Referring to FIGS. 5-8, at least a distal portion of electrically-insulative shaft 210 is formed from outer, intermediate, and inner tubes 250, 260, 270, respectively, concentrically arranged about one another. In embodiments, the entire electrically-insulative shaft 210 is formed from outer, intermediate, and inner tubes 250, 260, 270, respectively. In other embodiments, a proximal portion of electrically-insulative shaft 210 is formed from outer and inner tubes 250, 270, respectively, from intermediate tube 260, or via another combination of tubes 250, 260, 270 and/or other components.

Outer and inner tubes 250, 270, respectively, are formed from an electrically-insulative material such as, for example, a composite material, e.g., PTFE. Intermediate tube 260 is formed from an electrically-conductive material such as, for example, a metal, e.g., stainless steel. Distal ends 252, 272 of outer and inner tubes 250, 270, respectively, extend distally beyond distal end 262 of intermediate tube 260. Distal ends 252, 272 of outer and inner tubes 250, 270, respectively, are joined to one another in side-by-side relation along a longitudinally-extending joint 256, e.g., via welding, adhesion, or other suitable process, to enclose distal end 262 of intermediate tube 260 between outer and inner tubes 250, 270, respectively, thus electrically-insulative intermediate tube 260 from the outer, inner, and distal surroundings of electrically-insulative shaft 210. Intermediate tube 260 may define a rounded annular distal edge 264 to inhibit annular distal edge 264 from puncturing or otherwise damaging outer tube 250, inner tube 270, or joint 256 during manufacture and/or use.

The proximal ends of outer and inner tubes 250, 270 may extend proximally beyond the proximal end of intermediate tube 260 and may be joined similarly as detailed above or in any other suitable manner. Alternatively, the proximal ends of tubes 250, 260, 270 may be aligned with one another or the proximal end of intermediate tube 260 may extend proximally beyond the proximal ends of outer and inner tubes 250, 270. Regardless of the particular configuration, the proximal ends of tubes 250, 260, 270 may be secured to one another and/or other components of surgical instrument 10 (FIG. 1) in any suitable manner.

Intermediate tube 260 of electrically-insulative shaft 210 provides bending strength suitable to permit bending, e.g., up to 35 degrees from the longitudinal axis, of electrically-insulative shaft 210 and serves as an electrical shield, while outer and inner shafts 250, 270 and the joined distal ends 252, 272 thereof forming joint 256 electrically insulate intermediate tube 260 from the inner, outer, and distal surroundings of electrically-insulative shaft 210.

The annular gap 280 defined between outer and inner shafts 250, 270 to accommodate intermediate tube 260 therebetween defines a width "W1" that is sufficiently greater (e.g., at least 10% greater) than a thickness "T1" of intermediate tube 260 such that, in the fully assembled state of electrically-insulative shaft 210, a radial space exists between intermediate tube 260 and inner shaft 250 and/or between intermediate tube 260 and outer shaft 270.

With respect to the manufacture of electrically-insulative shaft 210, tubes 250, 260, 270 are manufactured independently. Thereafter, the distal ends 252, 272 of outer and inner tubes 250, 270, respectively, are joined to one another to form joint 256, e.g., via welding, adhesion, or other suitable process. Intermediate tube 260 is then inserted between outer and inner tubes 250, 270 from the proximal ends of outer and inner tubes 250, 270 until intermediate tube 260 is positioned in abutting relation or close proximity to joint 256. Alternatively, intermediate tube 260 may first be positioned between outer and inner tubes 250, 270 and the distal ends 252, 272 of outer and inner tubes 250, 270, respectively, thereafter joined to one another to form joint 256. The proximal ends of the outer and inner tubes 250, 270 may likewise be joined to enclose the proximal end of intermediate tube 260, or the proximal ends of tubes 250, 260, 270 may be secured to one another and/or other components in any other suitable manner.

Figure 9:
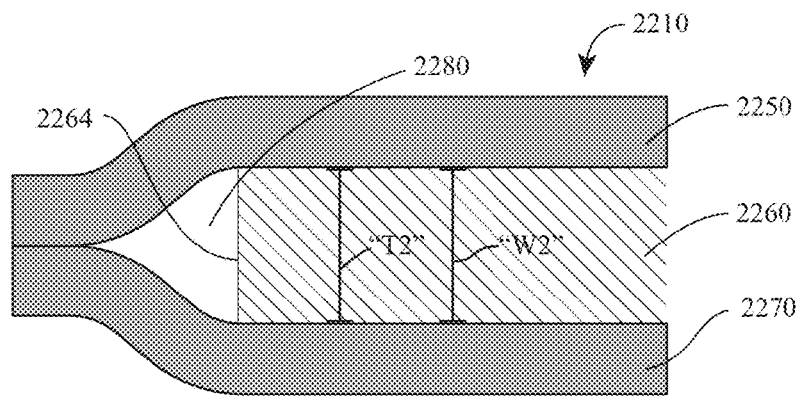
FIGS. 9-11 are longitudinal, cross-sectional views of portions of other electrically-insulative shafts provided in accordance with the present disclosure and configured for use with the surgical instrument of FIG. 1.

Turning to FIG. 9, another embodiment of an electrically-insulative shaft 2210 is shown. Electrically-insulative shaft 2210 is similar to electrically-insulative shaft 210 (FIGS. 5-8) and includes outer, intermediate, and inner tubes 2250, 2260, 2270, respectively, concentrically arranged about one another. However, electrically-insulative shaft 2210 differs from electrically-insulative shaft 210 (FIGS. 5-8) in that the annular gap 2280 defined between outer and inner shafts 2250, 2270 to accommodate intermediate tube 2260 therebetween defines a width "W2" that is sufficiently similar (e.g., less than 10% greater) than a thickness "T2" of intermediate tube 2260 such that, in the fully assembled state of electrically-insulative shaft 2210, intermediate tube 2260 substantially fully occupies gap 2280 so no radial space or a minimal radial space exists between intermediate tube 2260 and inner shaft 2250 or between intermediate tube 2260 and outer shaft 2270. Intermediate shaft 2260 also includes a cut annular distal edge 2264 that is not rounded, although annular distal edge 2264 of intermediate shaft 2260 may alternatively be rounded similar to rounded annular distal edge 264 of intermediate shaft 260 of electrically-insulative tube 260 (see FIG. 7).

Figure 10:
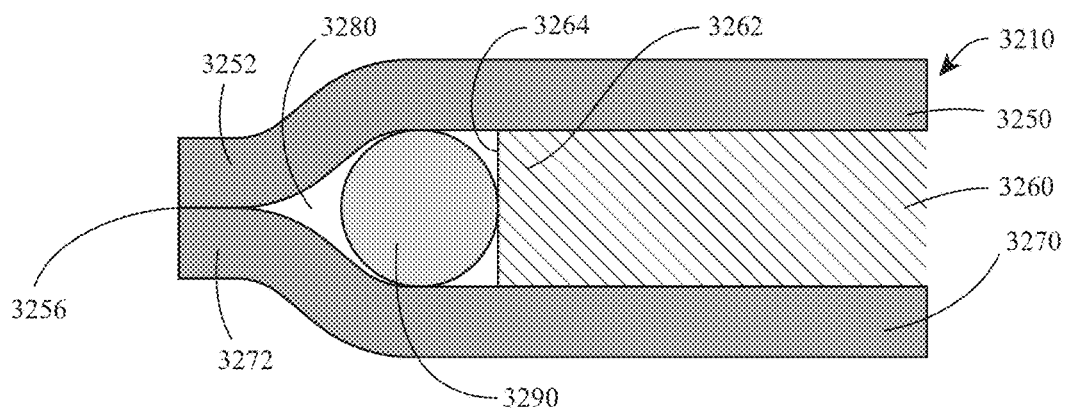

Referring to FIG. 10, another embodiment of an electrically-insulative shaft 3210 is shown. Electrically-insulative shaft 3210 may be similar to electrically-insulative shaft 210 (FIGS. 5-8) or electrically-insulative shaft 2210 (FIG. 9) and includes outer, intermediate, and inner tubes 3250, 3260, 3270, respectively, concentrically arranged about one another. Electrically-insulative shaft 3210 further includes an O-ring 3290 disposed within the annular gap 3280 defined between outer and inner tubes 3250, 3270 and positioned between distal end 3262 of intermediate tube 3260 and the joint 3256 defined by joined distal ends 3252, 3272 of outer and inner tubes 3250, 3270, respectively. O-ring 3290 helps maintain intermediate tube 3260 in position between outer and inner tubes 3250, 3270 and inhibits contact between annular distal edge 3264 of intermediate tube 3260 and joint 3256 or distal ends 3252, 3272 of outer and inner tubes 3250, 3270, respectively.

Figure 11:
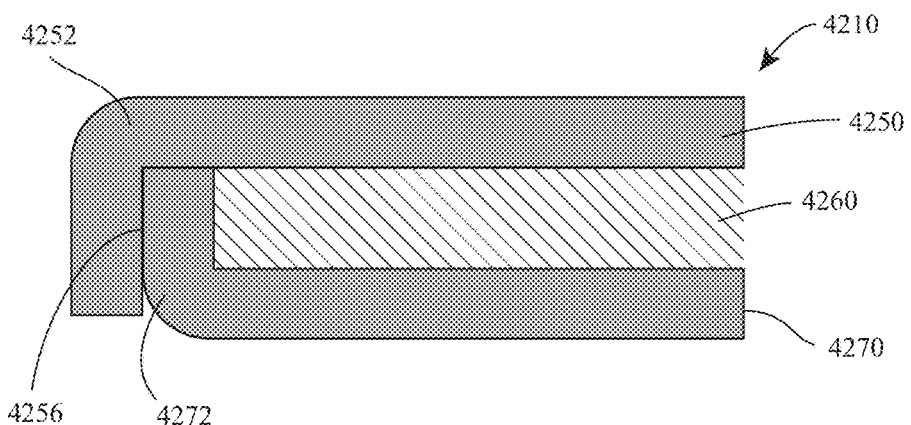

With reference to FIG. 11, another embodiment of an electrically-insulative shaft 4210 is shown. Electrically-insulative shaft 4210 may be similar to electrically-insulative shaft 210 (FIGS. 5-8), electrically-insulative shaft 2210 (FIG. 9), or electrically-insulative shaft 3210 (FIG. 10) and includes outer, intermediate, and inner tubes 4250, 4260, 4270, respectively, concentrically arranged about one another. Electrically-insulative shaft 4210 differs from the above-detailed electrically-insulative shafts in that, rather than the distal ends of the outer and inner tubes joined in side-by-side relation along a longitudinally-extending joint, distal ends 4252, 4272 of outer and inner tubes 4250, 4270 are folded transversely in opposite directions relative to one another to meet along a transversely-extending joint 4256. Distal ends 4252, 4272 may be joined via welding, adhesion, or other suitable process to form joint 4256. Further, distal end 4272 of outer tube 4270 may be folded over distal end 4252 of inner tube 4250, as illustrated, or, alternatively, distal end 4252 of inner tube 4250 may be folded over distal end 4272 of outer tube 4270.

From the foregoing and with reference to the various drawing figures, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrically-insulative shaft for an energy-based surgical instrument, comprising:
    an outer tube formed from an electrically-insulative material;
    an inner tube formed from an electrically-insulative material; and
    an intermediate tube disposed between the outer and inner tubes, the intermediate tube formed from an electrically-conductive material and being electrically isolated within the outer and inner tubes,
    wherein distal ends of the outer and inner tubes extend beyond a distal end of the intermediate tube and are joined to one another to enclose the distal end of the intermediate tube therebetween.

2. The electrically-insulative shaft according to claim 1, wherein the distal ends of the outer and inner tubes are joined along a longitudinally-extending joint.

3. The electrically-insulative shaft according to claim 1, wherein the distal ends of the outer and inner tubes are joined along a transversely-extending joint.

4. The electrically-insulative shaft according to claim 1, further comprising an O-ring disposed between the outer and inner tubes and between the distal end of the intermediate tube and the joined distal ends of the outer and inner tubes.

5. The electrically-insulative shaft according to claim 1, wherein a radial space is defined between at least one of the intermediate tube and the inner tube or the intermediate tube and the outer tube.

6. The electrically-insulative shaft according to claim 1, wherein the intermediate tube substantially fully occupies an annular gap between the inner and outer tubes.

7. The electrically-insulative shaft according to claim 1, wherein the outer and inner tubes are formed from PTFE and wherein the intermediate tube is formed from stainless steel.

8. The electrically-insulative shaft according to claim 1, further comprising a body portion having a first diameter, a distal portion having a second diameter larger than the first diameter, and an annular step disposed between the body portion and the distal portion, the annular step having a varying diameter transitioning from the first diameter to the second diameter, the distal portion including the outer, intermediate, and inner tubes.

9. A surgical instrument, comprising:
    a housing;
    at least one electrode operably coupled to the housing and configured to supply energy to tissue; and
    an electrically-insulative shaft extending at least partially between the housing and the at least one electrode, the electrically-insulative shaft including:
    an outer tube formed from an electrically-insulative material;
    an inner tube formed from an electrically-insulative material; and
    an intermediate tube disposed between the outer and inner tubes, the intermediate tube formed from an electrically-conductive material and being electrically isolated within the outer and inner tubes from the remainder of the surgical instrument,
    wherein distal ends of the outer and inner tubes extend beyond a distal end of the intermediate tube and are joined to one another to enclose the distal end of the intermediate tube therebetween.

10. The surgical instrument according to claim 9, wherein the at least one electrode includes a monopolar electrode.

11. The surgical instrument according to claim 9, wherein the at least one electrode includes a pair of bipolar electrodes.

12. The surgical instrument according to claim 9, wherein the distal ends of the outer and inner tubes are joined along a longitudinally-extending joint.

13. The surgical instrument according to claim 9, wherein the distal ends of the outer and inner tubes are joined along a transversely-extending joint.

14. The surgical instrument according to claim 9, further comprising an O-ring disposed between the outer and inner tubes and between the distal end of the intermediate tube and the joined distal ends of the outer and inner tubes.

15. The surgical instrument according to claim 9, wherein a radial space is defined between at least one of the intermediate tube and the inner tube or the intermediate tube and the outer tube.

16. The surgical instrument according to claim 9, wherein the intermediate tube substantially fully occupies an annular gap between the inner and outer tubes.

17. The surgical instrument according to claim 9, wherein the outer and inner tubes are formed from PTFE and wherein the intermediate tube is formed from stainless steel.

18. The surgical instrument according to claim 9, further comprising an elongated shaft assembly including a fixed outer tube extending distally from the housing, and the electrically-insulative shaft includes a body portion and a distal portion extending distally from the body portion, the body portion disposed within the fixed outer tube and the distal portion disposed distally beyond a distal end of the fixed outer tube, the distal portion including the outer, inner, and intermediate tubes.

19. A method of manufacturing an electrically-insulative shaft for a surgical instrument, comprising:
    providing an electrically-insulative outer tube, an electrically-insulative inner tube, and an electrically-conductive intermediate tube;
    joining distal ends of the outer tube and the inner tube with one another to form a joint;
    inserting the intermediate tube into an annular gap defined between the outer and inner tubes such that the distal ends of the outer and inner tubes extend beyond a distal end of the intermediate tube and enclose the distal end of the intermediate tube therebetween; and
    enclosing a proximal end of the intermediate tube to electrically isolate the intermediate tube within the outer and inner tubes.

20. The method according to claim 19, wherein the distal ends of the outer tube and inner tube are joined with one another to form the joint prior to inserting the intermediate tube into the annular gap.

21. The method according to claim 19, wherein the distal ends of the outer tube and inner tube are joined with one another to form the joint after inserting the intermediate tube into the annular gap.

22. The method according to claim 19, wherein the distal ends of the outer tube and inner tube are joined with one another to form the joint such that the joint extends in one of a longitudinal direction or a transverse direction.

* * * * *